United States Patent [19]

Lee

[11] Patent Number: 5,003,296

[45] Date of Patent: Mar. 26, 1991

[54] INFUSION APPARATUS WITH ALARM MEANS

[76] Inventor: Horng-Shu Lee, P.O. Box 55-1670, Taipei, Taiwan

[21] Appl. No.: 535,909

[22] Filed: Jun. 8, 1990

[51] Int. Cl.$^5$ ............................................. G08B 21/00
[52] U.S. Cl. ............................ 340/618; 128/DIG. 13; 604/31
[58] Field of Search ............... 128/DIG. 13; 340/618; 604/31

[56] References Cited

U.S. PATENT DOCUMENTS 3,992,706  11/1976  Tunney et al. ...................... 340/618
4,237,878  12/1980  Kobayashi et al. ........ 128/DIG. 13
4,378,014   3/1983  Elkow ........................ 128/DIG. 13

Primary Examiner—Joseph A. Orsino
Assistant Examiner—Jill Jackson

[57] ABSTRACT

An infusion alarm includes an infusion bag formed between an infusion bottle and a needle or cannula insertable in a patient body, and an exhausting sensor having two leaves pivotally connected with each other for resiliently clamping the infusion bag having two contactors respectively connected to two poles of a power source connected to an alarm, whereby when the infusion liquid is being dripped to be almost exhausted as injected to a patient's body, the two leaves of the sensor originally separated by the clamped infusion bag may be restored to close the two contactors for sounding the alarm and alerting a nurse for renewing the infusion liquid.

1 Claim, 2 Drawing Sheets

INFUSION APPARATUS WITH ALARM MEANS

BACKGROUND OF THE INVENTION

When a patient is administered by intravenous injection, an infusion bottle filled with nutritive liquid or additive is dripped into the patient's body through a tube. It should always be watched by a nurse or patient's family to prevent the exhausting of liquid in the bottle. Such a monitoring job may sometimes be neglected especially, when it is at mid night, by a nurse who may be very sleepy or tired. By applying a photoelectric sensor for monitoring the liquid level in the infusion bottle, it requires higher cost and expense for installing such an electronic system. By applying other detecting methods such as by putting a float sensor in the infusion bottle, the additional detecting articles may cause contamination or infection into the infusion system, hazardous to patient's health.

It is therefore expected to invent an alarm for warning an exhausting infusion bottle, which alarm is simply constructed and easily operated.

SUMMARY OF THE INVENTION

The object of the present invention is to provide an infusion alarm including an infusion bag formed between an infusion bottle and a needle or cannula insertable in a patient's body, and an exhaustion sensor having two leaves pivotally connected with each other for resiliently clamping the infusion bag having two contactors respectively connected to two poles of a power source connected to an alarm, whereby when the infusion liquid is being dripped to be almost exhausted as injected to a patient's body; the two leaves of the sensor originally separated by the clamped infusion bag may be restored to close the two contactors for sounding the alarm and alerting a nurse for renewing the infusion liquid.

DETAILED DESCRIPTION

Figures 1, 2:
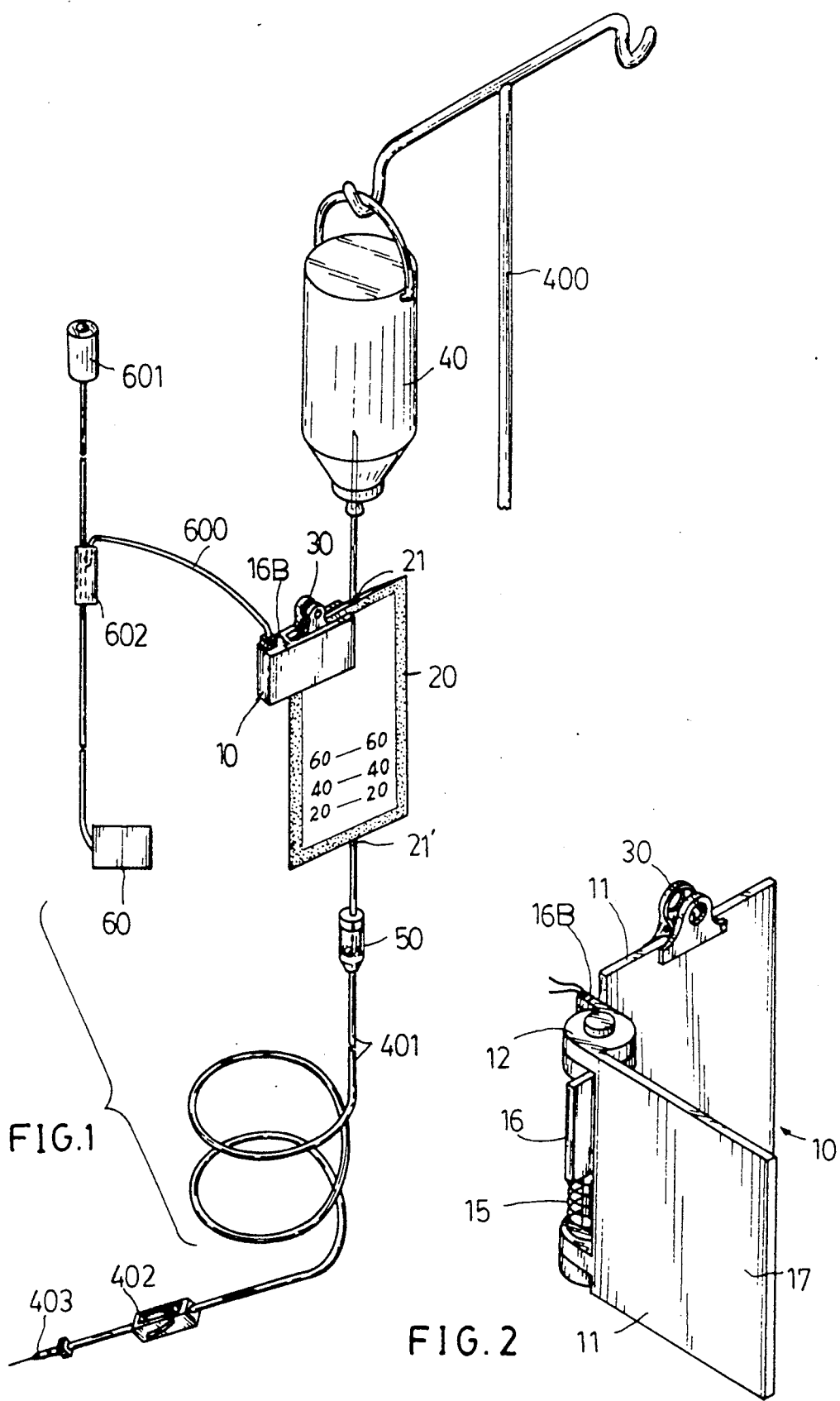
FIG. 1 is an illustration showing an infusion system in accordance with the present invention.
FIG. 2 shows an exhaustion sensor of the present invention.

The present invention comprises: an exhaustion sensor 10, an inflatable infusion bag 20, an infusion bottle 40, and an alarm means 60.

The infusion bottle 40 is hanged on a stand 400 for filling nutritive liquid, additive, or medicine therein having an upper leading needle connected to the infusion bag 20 for flowing the liquid inside the bottle 40 into the bag 20. A lower tube 21' connected to a lower portion of the bag 20 for directing the liquid into a drip display tube 50, a delivery tube 401 for injecting or infusing the liquid into a patient's body through a needle 403. A dripping adjuster 402 is provided to adjusting the dripping or infusion rate of the infusion system. If for blood transfusion purpose, the infusion bottle 40 may be substituted with a blood bag.

The inflatable infusion bag 20 may be made of flexible plastic materials and is clamped on one leaf 11 of the sensor 10 by a clip 30 secured to the leaf 11. The clip 30 is spring loaded so that it can be depressed for releasing the bag 20 for the renewal of fresh bag 20 for continuous injection or infusion.

The exhaustion sensor 10 includes: two clamping leaves 11, 11 pivotally connected with each other by a bolt or a pin 14 pivoted through a plurality of lugs 12 protuding inwardly from each leaf 11 by passing the pin or bolt 14 through the holes 13 formed in the lugs 12, a restoring spring 15 disposed around the pin or bolt 14 for normally restoring the two leaves 11 for resiliently clamping the bag 20 therebetween, two electric conducting plates 16 respectively formed on each inner portion of each leaf 11 each conducting plate 16 having a contractor 16A, 16A' formed on the plate 16, and a flexible insulating jacket 17 covering the leaves 11 for preventing electric shock accident. The sensor 10 may be also be made of plastic materials, except the conducting plate 16 or contactor 16A, by integrated molding process.

Each conducting plate 16 or contactor 16A or 16A' is electrically connected to a pole of a power source. For instance, one contactor 16A of one leaf 11 is connected to a positive pole or terminal of a power source connected to the alarm means 60 and the other contactor 16'A of the other leaf 11 is connected to a negative pole of the power source.

Figure 4:
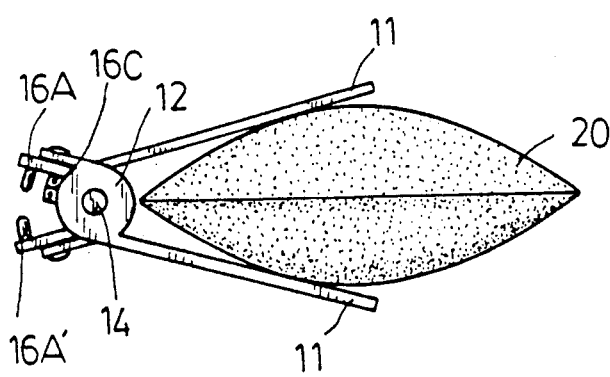
FIG. 4 is a top view illustration having the sensor normally clamping the infusion bag opening the alarm circuit in accordance with the present invention.

As shown in FIG. 4, 5, a socket 16C is secured to one lug 12 of one leaf 11 having a positive clip electrically connected with the positive contactor 16A and having a negative clip electrically connected to a negative contactor 16A' when closing the two leaves 11 when the bag 20 is slightly shrinked due to the exhausting of liquid filled therein. The socket 16c is connected to a plug 16B which is connected by wires 600 to an alarm means 60 provided in a nurse station which may be connected in parallel with any existing bell or emergency call system 601 having push botton formed on each patient's bed by means of a splitting connector 602 as shown in FIG. 1.

Figure 5:
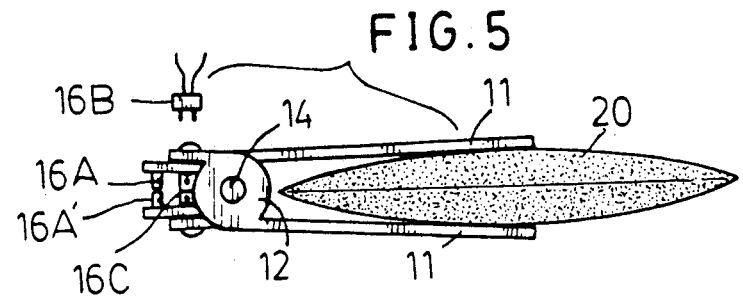
FIG. 5 is a top view showing the closing leaves of the sensor for actuating the alarm of the present invention.

In using the present invention, when the infusion liquid from the bottle 40 is dripped into the bag 20 for expanding the bag 20 as shown in FIG. 4 to open the contactors 16A, 16A' without actuating the alarm means 60, and when the bag 20 is being exhausted due to the continuous dripping, the bag 20 will be shrinked and the two leaves 11 of the sensor 10 will be resiliently restored by the spring 15 to be flattened from FIG. 4 to FIG. 5 to close the two contactors 14A, 16A' to close an alarm circuit having a buzzer of the alarm means 60 for sounding the alarm and alerting the nurse for renewing a fresh bottle 40. The present invention may be designed to allow a minimum liquid quantity or level existing in the bag 20, for instance, a final buffer quantity of 5 minutes to ensure a real liquid content in the infusion system. By the way, the present invention may prevent an absolute exhausting of infusion liquid in an infusion system or apparatus to prevent any hospital trouble, such as backflow of blood flowed from a patient's body frozen to clog the needle when there is no dripping flow from the infusion system.

Figure 3:
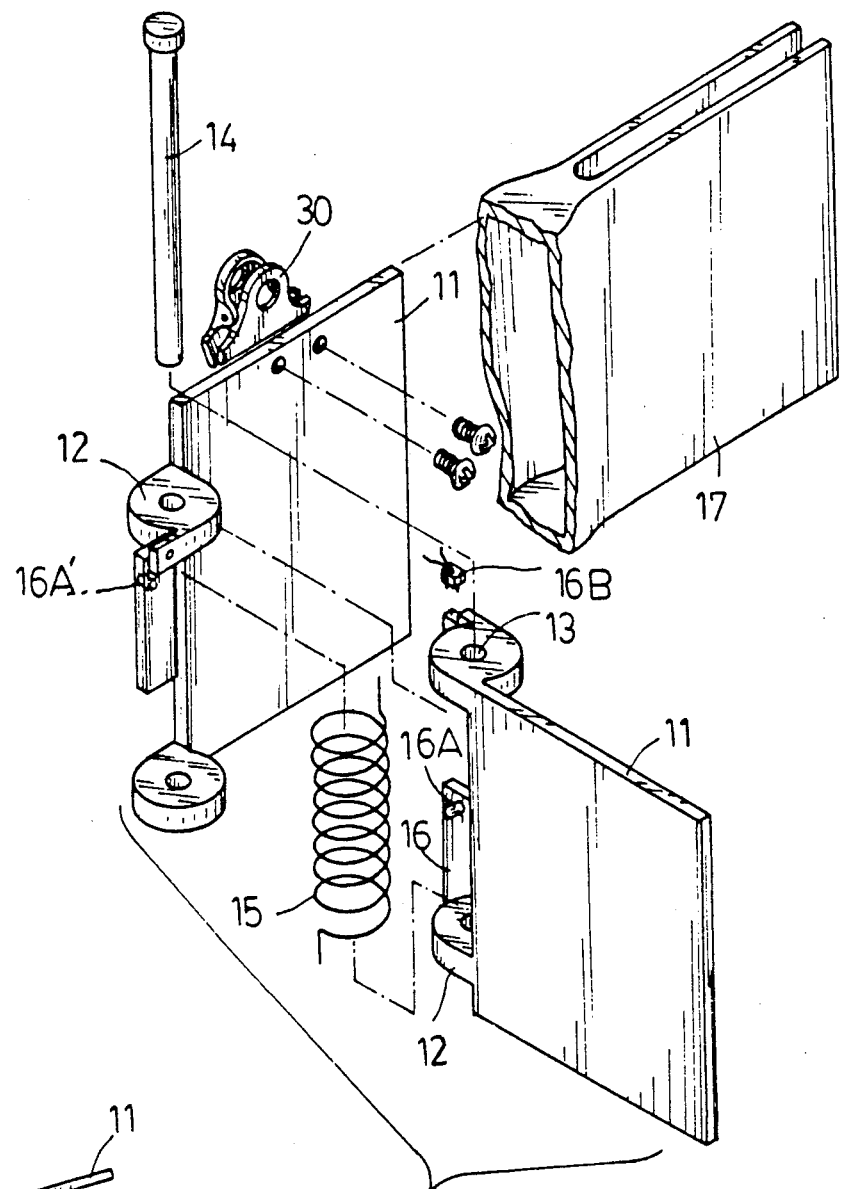
FIG. 3 is an exploded view of the sensor of the present invention.

One right conducting plate 16 may be secured to a lower lug of two lugs 12 of the right leaf 11, whereas the other left conducting plate 16 may be secured to an upper lug of two lugs 12 of the left leaf 11 as shown in FIG. 3.

Of course, the lugs 12 may be omitted in this invention and the two leaves 11 may be pivotally connected by a hinge (not shown), wherein a pair of electric contactors may be respectively formed on two inner portions of the two leaves 11 facing with each other and operatively contacted when closing the two leaves due to the shrinkage of the clamped bag 20 when exhausted for closing the alarm circuit for sounding the alarm. The sensing and alarming circuit of the present invention may be modified by those skill in the art without departing from thre spirit of this invention.

I claim:

1. An infusion apparatus comprising:
   an infusion bottle filed with infusion liquid hanged on a stand; an inflatable infusion bag connected between said infusion bottle and an injection needle or cannula inserted into a patient's body;
   an exhaustion sensor including two clamping leaves pivotally connected with each other and resiliently restored for normally clamping said infusion bag therebetween when said bag receives the dripping liquid dripped from said infusion bottle to expand the bag, having a pair of electric contactors respectively formed in two inner portions of said two leaves normally separated with each other, each said electric contactor electrically connected to anyone pole of two poles of a power source; and
   an alarm means having an alarm circuit provided with a buzzer connected between said two poles of said power source, said alarm means being actuated when the infusion bag is exhausted to close the two leaves and the two electric contactors for closing the alarm ciruit fo sounding the alarm means for alerting an exhaustion of said infusion bag, the improvement which comprises:
   said exhaustion sensor including said two clamping leaves pivotally connected by a pin or bolt passing through a plurality of lugs protuding inwardly from said two leaves, a first conducting plate having a first electric contactor formed thereon secured on lower lug of two first lugs of the first clamping leaf, and a second conducting plate having a second electric contactor formed on said second plate secured to an upper lug of two second lugs of the second clamping leaf, said two conducting plates and electric contactors normally opened when said two leaves are separated by an expanded infusion bag clamped by two said leaves, and operatively closed to close said alarm circuit when said infusion bag is shrinked by exhausting its dripping liquid to close said two leaves, and
   said infusion bag clamped on one said leaf by a clip secured on said leaf.

* * * * *